United States Patent [19]

Kitchen, III et al.

[11] Patent Number: 4,556,326

[45] Date of Patent: Dec. 3, 1985

[54] METHOD FOR TESTING AND TREATING STORED FUEL

[76] Inventors: George H. Kitchen, III; Nancy E. Kitchen, both of 646 Lakeview Cir., Rio Rancho, N. Mex. 87124

[21] Appl. No.: 658,764

[22] Filed: Oct. 9, 1984

[51] Int. Cl.[4] ............................................. G01N 25/00
[52] U.S. Cl. ..................................... 374/45; 250/373; 73/61 R; 436/155
[58] Field of Search ........................ 374/17, 20, 16, 45, 374/53, 54, 57; 250/373; 73/61 R; 436/60, 139, 143, 155, 164

[56] References Cited

U.S. PATENT DOCUMENTS

| | | | |
|---|---|---|---|
| 3,059,467 | 10/1962 | Meguerin et al. | 374/45 |
| 3,457,772 | 7/1969 | Chassagne et al. | 374/17 |
| 3,695,847 | 10/1972 | Hirschfeld | 436/164 |

Primary Examiner—Charles Frankfort
Assistant Examiner—Thomas B. Will

[57] ABSTRACT

A method for testing and treating distillate fuel being stored for long periods of time for emergency power generation applications and the like, including measuring the percent transmittance of a fuel sample with ultraviolet before and after heating at a preselected temperature below the boiling range of the distillate fuel for a sufficient period of time to accelerate polymerization where the sample is made to reach such preselected temperature within about five minutes; and comparing the percent transmittance measurements to determine the suitability of the fuel for continued storage with or without the addition of further polymerization inhibitors and/or depolymerizers.

14 Claims, 4 Drawing Figures

FIG. 1 % TRANSMISSION AT 527 NANOMETERS

METHOD FOR TESTING AND TREATING STORED FUEL

BACKGROUND OF THE INVENTION

This invention relates to a method for testing and treating fuel oils such as diesel fuel which needs to be stored or has been stored for long periods of time and in particular in fuel storage situations required for emergency stand-by motor generators.

Current diesel fuels generally require more refining, i.e. catalytic cracking, than heavier oils. The conversion of many standby emergency power facilities to the use of diesel fuel has therefore produced several new problems relating to the inherent instability of such fuels when stored for long periods of time.

Distillate fuels, including diesel fuels are prone to deteriorate during prolonged storage by forming polymerizates which agglomerate into what is referred to as sludge which can clog fuel lines, filters, and fuel injectors preventing, for example, the reliable operation of a diesel engine. In addition, water in the fuel and in the form of condensates in a partially filled distillate fuel storage tank will, by itself or in combination with fuel components, attack the metal of the tank forming rust which also promotes the polymerization of components in the fuel.

In addition, new regulations promulgated by the Environmental Protection Agency have recognized the problem of rusting tanks and now require measures to prevent contamination of ground water which can occur from fuel leaking underground from tanks that have been perforated by rust.

Likewise, sludge formation can be accelerated by the growth of bacteria in the fuel.

Therefore, a wide variety of polymerization inhibitors have been employed. Such inhibitors were generally capable of retarding the formation of sludge and newer compositions, such as described in U.S. patent application, Ser. No. 621,073, filed June 15, 1984, by George Holcom Kitchen, III entitled "Fuel Additive", have shown the additional capability of dispersing agglomerates, polymerizates and sludge once formed. It is known that the deterioration of fuel oils involves polymerization reactions resulting in the agglomeration of macroscopic polymerizates into sludge. Although this reaction may be effected by the presence of oxygen, additives containing antioxidants, such as hindered phenols or diamines of the types used in gasolines as gum inhibitors, are not totally effective for the purpose of preventing the polymerization mechanisms. The additive materials, in addition to the foregoing, should also have rust-preventive properties in order to keep the fuel tanks clean and dry, and to reduce or eliminate rust formation in the tanks.

The additive materials should also inhibit the propagation of bacteria. The kinds of bacteria that grow in stored fuels thrive on nitrogen, sulfur, and phosphorus, as well as iron, generally in the form of its oxides. Of course, the elimination of materials in the fuel tank that contain nitrogen, sulfur or phosphorous is difficult to achieve in any practical situation.

For all of the foregoing reasons, various additive materials are utilized to prolong the storage life of distillate fuels.

Even the best of these prior attempts to stabilize distillate fuels against substantial deterioration during long-term storage were only effective for limited periods of time. Prolonged storage situations still requires routine monitoring and corrective action to reduce agglomeration, rust and the like in order to insure proper engine performance from the stored fuel when its use is required in emergency situations.

In order to determine the continued efficiency of the stored fuel, many different testing procedures were devised to help the user determine whether fuel stored for prolonged periods of time will be capable of performing effectively, when required.

A widely used test has been a variation of the colorstability test in Federal Specification VV-K-211 Kerosene. Generally, this test specified heating a sample of the fuel and observing a color change which was relatable, in some degree to the current condition of the fuel and its ability to withstand further storage without replacement or the addition of further additives. In addition to observing the color change, the amount of filterable sludge and sediment also had to be measured. Another test procedure used was a prolonged version of the Gulf Oil Company's Fuel Corrosion of Steel Test. This test, developed by Bell Laboratories, has been correlated against fuels actually stored in a stand-by power fuel tank. These tests were run at 210° F. until an observable amount of sludge has formed. This test is essentially an accelerated heat-stability test and is typically run in the absence of water. A second test was run at 120° F. over water in the presence of 1020 steel strip. This portion of the test is concluded only after 12 weeks have lapsed or when an observable quantity of rust and sludge has been deposited.

The accelerated heat-stability portion of the foregoing test was comparatively quick and useful for screening out poor additive performance in the selection of additives for use and to a limited extent, for routinely monitoring the condition of actual stored fuel. But, because water is not present in this test, it was not capable of differentiating between those additives that are either not effective rust inhibitors, or not suitable for protecting the fuels when stored in contact with water and steel, from those that are effective under storage conditions where water and steel (and therefore rust) are present. It is precisely these conditions that are the most important in long-term storage since stand-by fuels are frequently in contact with metal and condensate water, and the presence of particulate rust may be often as severe a problem as sludge formation. Even the 12 week stability-and-rust test, which was designed to evaluate these effects did not provide a timely method for monitoring storage conditions and problems.

Because of the importance of stabilizing the fuels for extended periods of time, i.e. up to 20 years, with the fuels in contact with metal and water, it is essential that the performance of the additives also be evaluated properly for use before and during storage.

In another previously used test, artificially aged fuel is filtered and the residues measured by various means. A major problem associated with these tests was the presence of various sized polymers which caused errors in the amount of material retained on the filter pads as well as inordinately lengthening the time for filtration. The new refining technology coupled with the new crude sources has tended to aggravate this problem. Some experimenters have used finer filter paper, others have switched to membrane filters. Both of these changes recognized the presence of the described problem but do not solve it with respect to test speed. Other experimenters attempting to solve the foregoing problems have varied the method of introducing oxygen in the aging process, concentrating on oxidation as the principal mechanism of polymer generation. This also has met with only limited success.

As previously described, the additives previously employed have provided some measure of protection for stored fuel with respect to some of the major properties required, for the short-term.

For very long term storage however, it is essential that the inhibitor employed be capable of being employed both initially and during routine maintenance, if required, to depolymerize and disperse the sludge that is inevitably formed, such as described in U.S. Ser. No. 621,073 which is incorporated herein by reference. More timely results from test procedures are still required using such additives so that the test can be conducted at the site of the stored fuel and the necessary corrective action taken at that time.

It is also important that attempts to eliminate the problem of injector clogging at low temperature by the build-up of hydrocarbon waxes in the fuel by the use of additives containing solvents for these waxes does not compound injector scoring problems by reducing or eliminating the lubricity of the fuel. Over-zealous use of such previously used solvent-containing additives can, and often does produce service interruption due to the mechanical demands of the diesel engine, which can be pressed into prolonged service during emergencies.

Therefore, the combination of new refining technology and the use of new crude sources and the kinds of additives now available have produced a need for an improvement of the current fuel testing procedures.

It is therefore an objective of the present invention to provide a test procedure for stored distillate fuels which can be used at the site of the stored fuel at the time of routine maintenance which will give a timely indication of the condition of the fuel for its suitability for subsequent use and further storage thereby providing an opportunity to employ timely corrective action if required.

SUMMARY OF THE INVENTION

The foregoing objective is achieved according to this invention by the following apparatus and method. First, a small sample of stored fuel is taken from the storage tank, preferably less than 10 ccs, making certain that the technique of taking the sample does not disturb the water or sediment from the bottom of the tank. Preferably, in a routine maintenance program, the water is completely removed from the tank before a sample for testing is taken. The fuel sample is then heated in a predetermined manner to a high enough temperature, below the boiling point range of the fuel, for a sufficient period of time to accelerate the formation of macroscopic agglomerates by rapid polymerization. Typically, the sample is preferably heated to a temperature of from about 200° F. (93.3° C.) to about 340° F. (171.1° C.) for between about 3 minutes to about 90 minutes with the fuel reaching the selected temperature in 3–5 minutes. More preferably, the sample is heated within 5 minutes to a temperature of about 300° F. (148.9° C.) and held at that temperature for about 10 minutes.

The ultraviolet transmission characteristics of the fuel sample before heating and after heating and cooling is measured. Preferably, the transmission characteristics at a single wave length or single narrow band of wave lengths selected between 400 and 680 nanometers are used for these measurements. More preferably, the wave lengths around 572 nanometers is selected.

DETAILED DESCRIPTION OF THE INVENTION

Figure 1:
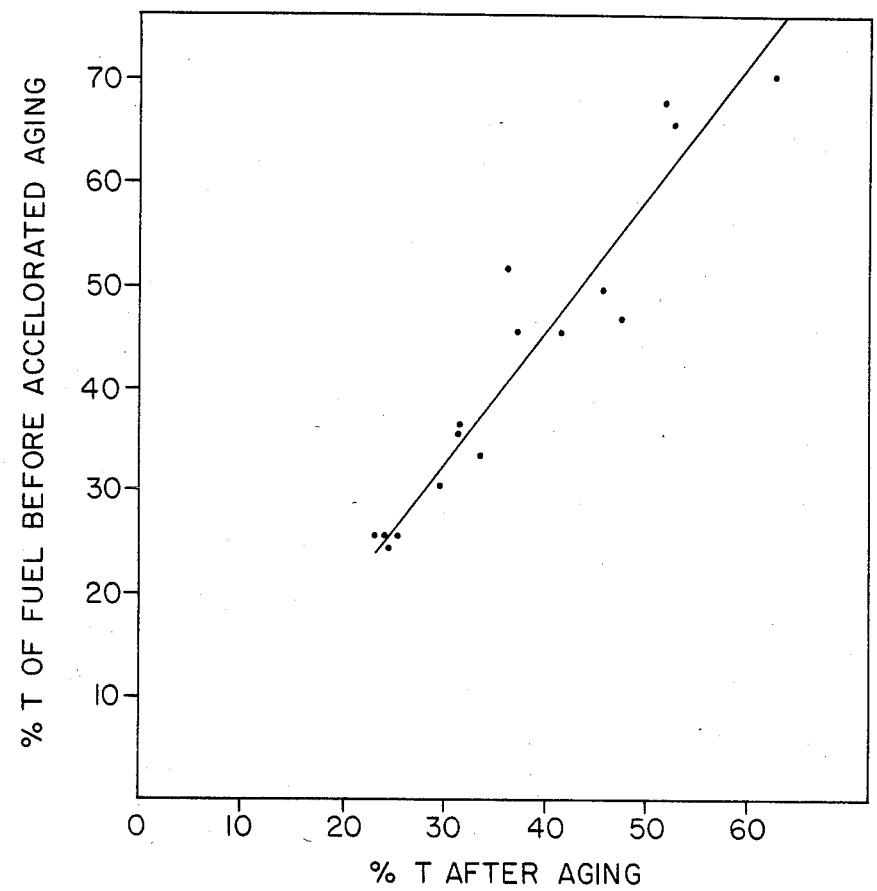
FIG. 1 is a plot of the percentage transmittance of a fuel sample before testing versus the percentage of change in transmittance after previous testing procedures.

An attempt was made to correlate the ultraviolet transmission characteristics of the fuel both before and after the accelerated aging using the old aging methods used in combination with the filtration of residue. The fuel samples were heated at 300° F. for 90 minutes in an air circulation oven and the percentage transmittance plotted for samples with additives and samples without additives. The results from such runs after specific time intervals are shown in FIG. 1. These results demonstrate that no correlation could be made between the samples based on the percentage of transmittance for ultraviolet before heating with the change in percentage transmittance produced by heating.

With a metal heater block designed so that each sample more quickly reached the 300° F. (148.9° C.) test temperature, different results were obtained. In general, it was determined that there was a good correlation between fuel that was known to contain an effective agglomeration preventing agent and actual fuel samples from various sources after extended storage periods. In particular, it was discovered that all of the samples underwent their greatest changes in percent transmittance within thirty (30) minutes of heating at 300° F. (148.9° C.). During these tests, all samples reached relatively constant though different values after ninety (90) minutes with the rate of change between thirty and ninety minutes showing a relatively shallow slope of curve. Plotted data from the testing of freshly prepared fuels with agglomerating inhibiting additives, while following the same general slope of curve, consistently exhibited a higher percentage transmittance throughout the treating time.

With the foregoing discovery, a heater design was tried which utilizes a relatively small sample of fuel in a well in a metal block which assured better heat transfer so that each sample reached the 300° F. (148.9° C.) test temperature in under five minutes. The temperature of the sample remained constant throughout the test and the post-heating transmittance data was taken after the samples had cooled back to ambient temperature. Typical results of this test procedure are shown in FIG. 2, wherein the fuel sample data for curve A represents a useful, polymerization inhibited fuel, while curves B, C, D and E show fuels in various stages of deterioration.

Figure 2:
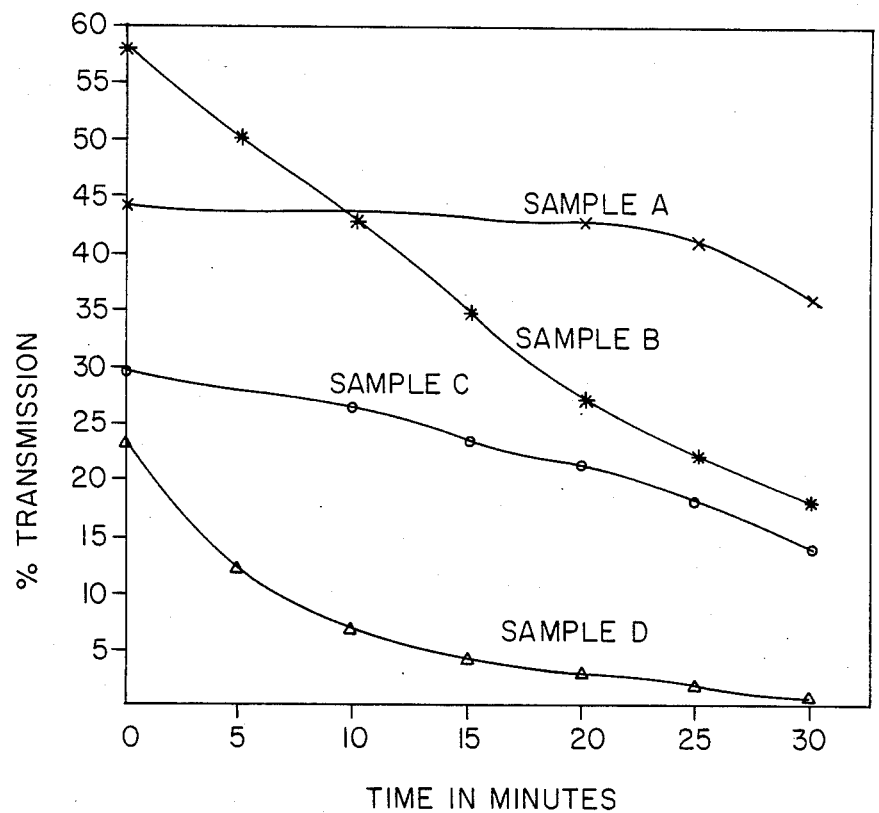
FIG. 2 is a plot of the percentage transmittance of fuel that has been treated with additives to inhibit polymerization and the formation of agglomerates during storage using the test described herein.
Figure 3:
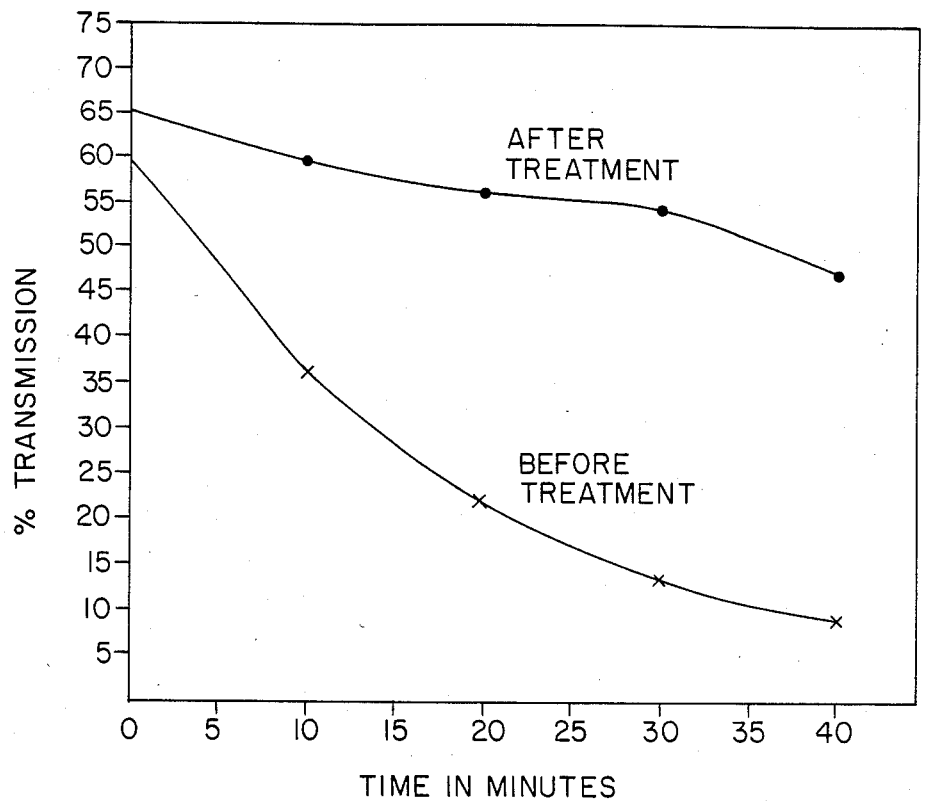
FIG. 3 is a plot of the percentage transmittance of the same aged fuel sample before and after the addition of inhibitor additives.
Figure 4:
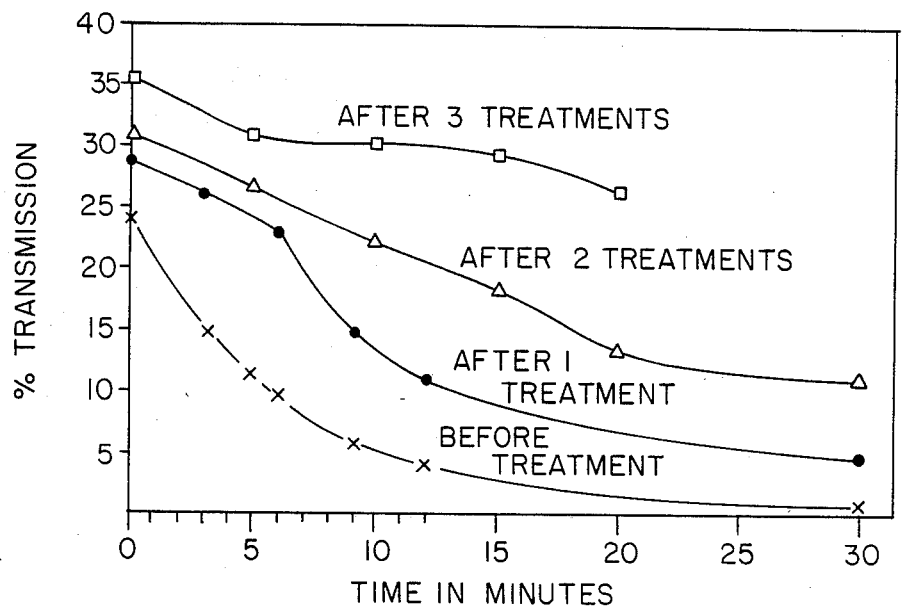
FIG. 4 is a plot comparing the percentage transmittance of uninhibited aged fuel and fuel samples after the addition of subsequent doses of additives for inhibiting agglomeration.

Further, testing was undertaken with fuel samples, such as curve B in FIG. 2 where depolymerization and dispersion had taken place due to the addition of predetermined amounts of additives capable of provoking such a change without producing a lack of lubricity. The effect of subsequent additions of the additive is shown in FIG. 3.

In this manner, the correlation is clearly shown, such that, a particular stored fuel can be successfully evaluated according to the testing procedure described, and corrective action taken to restore the fuel to a suitable condition for use by the addition of a proper additive in the appropriate amount.

In the field, the foregoing test can be accomplished with a minimum of sophisticated equipment. A small aluminum block oven, and a spectrophotometer, such as a Bausch and Lomb Spectronic 20 uv spectrophotometer can be employed. For convenience and speed, a small computer terminal of personal computer can be utilized with a program which generates the kinds of plots, shown herein, to provide the maintenance personnel with the necessary information for taking proper corrective action, if required. This and other maintenance functions can be provided on-site and with a data link to a central data processing source via phone lines or radio transmission, and instructions can be relayed to the maintenance personnel without the need for a return trip to the site before the next scheduled routine maintenance.

The invention described herein can be practiced in a wide variety of ways without departing from the scope of the claims herein, which are limited only by the prior art which is applicable thereto.

What is claimed is:

1. A method for testing samples of distillate fuels obtained from long-term storage tanks for such fuels comprising the steps of:
   (1) heating the fuel sample to a preselected test temperature within about 3 to about 5 minutes;
   (2) holding the fuel sample at a test temperature of from about 200° F. (93.3° C.) to about 340° F. (171.1° C.) for a sufficient period of time to accelerate the formation of agglomerates in the fuel sample;
   (3) cooling the fuel sample to ambient temperature;
   (4) measuring the percentage transmittance of ultraviolet through the fuel sample.

2. The method for testing fuel samples of claim 1 wherein the percentage transmittance of the fuel sample is measured with ultraviolet between 400 and 680 nanometers wavelength.

3. The method for testing fuel samples of claim 2 wherein the percentage transmittance is measured at a wave length of about 572 nanometers.

4. A method for testing distillate fuels during long-term storage to determine their suitability for subsequent use comprising the steps of:
   (1) measuring the ultraviolet transmittance of a fuel sample from such long-term storage;
   (2) heating the fuel sample to a preselected test temperature below the boiling point temperature range of said fuel sample within about 3 to about 5 minutes;
   (3) holding the fuel sample at said preselected test temperature for between about 3 minutes to about 90 minutes;
   (4) cooling the sample to ambient temperature;
   (5) measuring the percentage of ultraviolet transmittance of said cooled sample; and
   (6) comparing the percentage transmittance of the sample before heating with the percentage transmittance after heating.

5. The method of claim 4 wherein the percentage of ultraviolet transmittance through the sample before heating is measured at wave lengths between about 400 and 680 nanometers.

6. The method of claim 4 wherein the percentage of ultraviolet transmittance through the sample after heating is measured at wavelengths between about 400 and 680 nanometers.

7. The method of claim 4 wherein the percentage of ultraviolet transmittance of samples before and after heating is measured at about 572 nanometers.

8. The method of claim 7 wherein the fuel sample is heated within about 3 to about 5 minutes to a temperature in the range of from about 200° F. (93.3° C.) to about 340° F. (171.1° C.).

9. The method of claim 4 wherein the fuel sample is held at the preselected test temperature for about 10 minutes.

10. A method of treating fuel for long-term storage comprising the steps of:
    (1) measuring the ultraviolet transmission of a fuel sample from the fuel to be used for long-term storage;
    (2) heating the fuel sample to a preselected test temperature of from about 200° F. (93.3° C.) to about 340° F. (171.1° C.) within a time interval of from about 3 to about 5 minutes;
    (3) holding the fuel sample at said preselected test temperature for between about 3 minutes to about 90 minutes;
    (4) measuring the percentage of ultraviolet transmittance of the sample after heating;
    (5) comparing the percentage transmittance of the sample before heating with the percentage transmittance after heating;
    (6) adding polymerization inhibitor to the fuel in an amount sufficient to increase the percent transmittance of the sample after heating and addition of inhibitor to a pre-determined value above the measured percent transmittance before addition of said inhibitor.

11. The method of claim 10 wherein the percentage of ultraviolet transmittance through the sample before heating is measured at wave lengths between about 400 and 680 nanometers.

12. The method of claim 10 wherein the percentage of ultraviolet transmittance through the sample after heating is measured at wavelengths between about 400 and 680 nanometers.

13. The method of claim 10 wherein the percentage of ultraviolet transmittance of samples before and after heating is measured at about 572 nanometers.

14. The method of claim 10 wherein the fuel sample is held at the preselected test temperature for about 10 minutes.

* * * * *